United States Patent
Winston

[11] Patent Number: 5,853,290
[45] Date of Patent: Dec. 29, 1998

[54] ULTRASONIC TOOTH CLEANER

[76] Inventor: Ronald H. Winston, 256 Griffen Ave., New York, N.Y. 10583

[21] Appl. No.: 758,037

[22] Filed: Nov. 27, 1996

Related U.S. Application Data

[63] Continuation-in-part of Ser. No. 563,293, Nov. 28, 1995, Pat. No. 5,772,434.

[51] Int. Cl.⁶ ..................................................... A61C 1/07
[52] U.S. Cl. ............................................. 433/86; 433/119
[58] Field of Search ................................. 433/80, 87, 86, 433/141, 118, 119

[56] References Cited

U.S. PATENT DOCUMENTS

| | | | |
|---|---|---|---|
| Re. 30,536 | 3/1981 | Perdreaux, Jr. | 433/86 |
| 3,526,219 | 9/1970 | Balamuth | 433/119 X |
| 3,547,110 | 12/1970 | Balamuth . | |
| 3,636,947 | 1/1972 | Balamuth . | |
| 3,645,255 | 2/1972 | Robinson . | |
| 3,651,576 | 3/1972 | Massa . | |
| 3,924,335 | 12/1975 | Balamuth et al. | 128/24 A |
| 4,176,454 | 12/1979 | Hatter et al. . | |
| 4,331,422 | 5/1982 | Heyman . | |
| 4,370,131 | 1/1983 | Banko . | |
| 4,735,200 | 4/1988 | Westerman | 128/66 |
| 4,787,847 | 11/1988 | Martin et al. . | |
| 4,832,683 | 5/1989 | Idemoto et al. | 433/119 X |
| 5,286,192 | 2/1994 | Dixon . | |
| 5,531,597 | 7/1996 | Foulkes et al. | 433/119 |

OTHER PUBLICATIONS

Ultem Polyetherimide Resin Properties Guide (2 pages), undated.
Delrin Chemical description, pp. 201–203, undated.
Noryl Chemical description, p. 231, undated.
Lexan Chemical description, pp. 102–108, undated.

*Primary Examiner*—Nicholas D. Lucchesi
*Attorney, Agent, or Firm*—Darby & Darby

[57] ABSTRACT

An ultrasonic tooth cleaner having an elongated tip having multiple bends or a curved shape. This allows the operator to reach any surface or crevice in the oral cavity. The tips are formed of plastic materials that can withstand constant ultrasonic vibration in a range that is therapeutically beneficial.

13 Claims, 2 Drawing Sheets

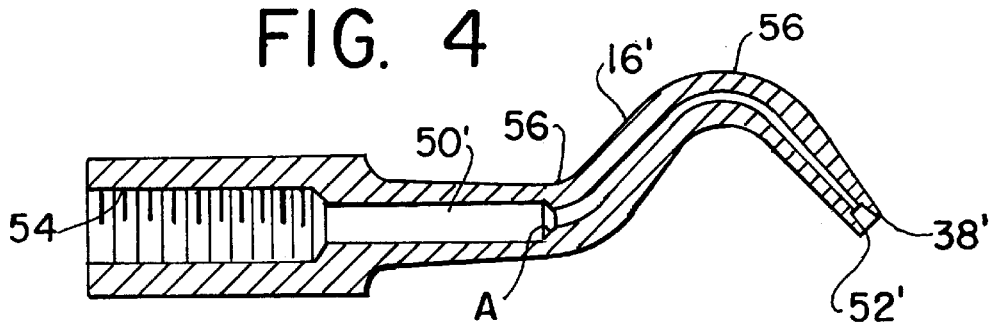
FIG. 4
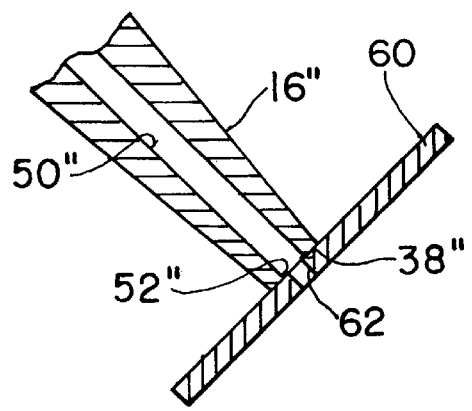
FIG. 5
FIG. 6
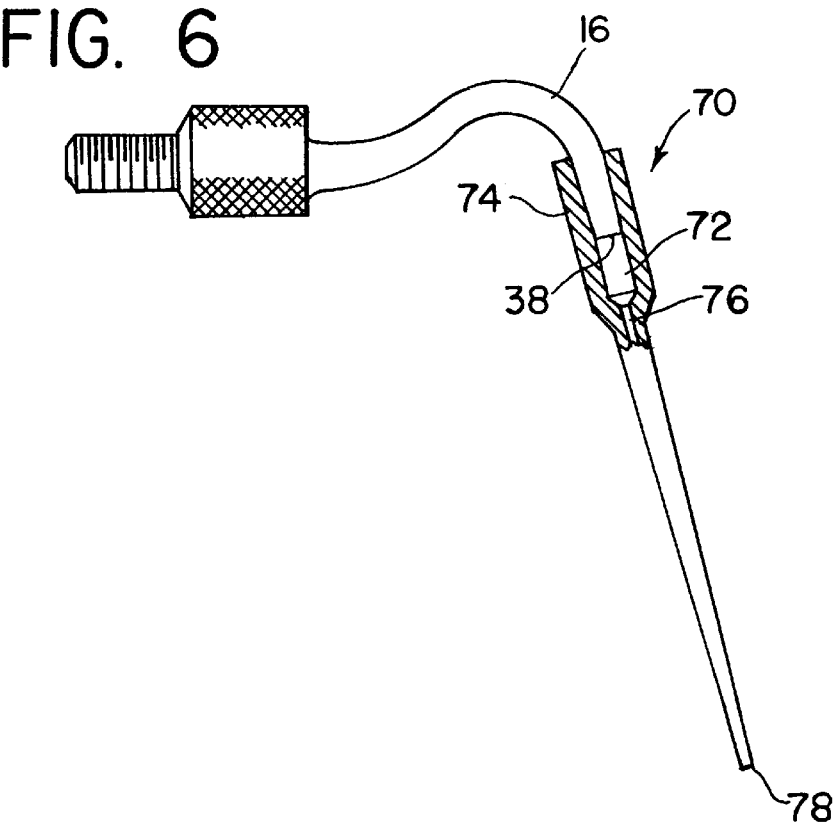

ULTRASONIC TOOTH CLEANER

This is a continuation-in-part of Ser. No. 08/563,293, filed Nov. 28, 1995 now U.S. Pat. No. 5,772,434, now pending.

FIELD OF THE INVENTION

This invention relates generally to devices for maintaining dental hygiene. More specifically, this invention relates to devices for ultrasonically removing deposits from tooth surfaces and ultrasonically providing therapeutic and other fluids thereto.

BACKGROUND OF THE INVENTION

The use of ultrasonic energy for removing deposits from tooth surfaces is known. Dentists employ ultrasonic energy to drive a metal scaling device in order to scrape away any deposits such as tartar, calculus and plaque. The metal tip of conventional devices makes it possible to use high frequency, high energy waves to break up even the hardest deposits on the teeth. Essentially, these devices rely on the known technique of physically scraping the deposits from the teeth.

The available ultrasonic energy decreases the force the dentist must apply by multiplying the scraping motions thousands-fold and by employing dynamic rather than static forces. However, these devices are impractical for home or personal use, where daily removal of dental plaque is essential for dental health and the forces provided by these devices are excessive for dental plaque removal. Moreover, conventional metal tips readily become hot and require substantial cooling which is usually done with a stream of continually flowing water. Furthermore, metal tips can be too easily mishandled when operating on oneself, which could lead to damage of the tooth surfaces or the gums. Without sterilization equipment or multiple costly metal tips, the device would also be usable by only one family member, as it is known that gingival bleeding often takes place with this type of cleaning. Such gingival bleeding would contaminate the tip and prevent its use by a second person.

An advance over these professional devices has been the use of ultrasonically oscillating water jets. By superimposing ultrasonic pulses onto a stream of liquid, various benefits can be gained. Cavitation caused by ultrasonic waves will tend to loosen or disintegrate soft deposits on a tooth, while the constant jet flushes away any debris. It is also possible to aim the jet at interdental areas, providing good coverage during cleaning. However, only relatively loose deposits can be removed with this type of device, depending on the type of liquid used. Often, gritty liquids are used to improve a grinding effect, but complete removal of deposits can be difficult to attain.

In U.S. Pat. No. 3,547,110, Balamuth discloses a device that attempts to combine features of both of the aforementioned types of prior art systems. A high velocity jet of liquid is pulsed at ultrasonic frequencies to create cavitations and disruption of the bonds (physical and/or chemical) between certain kinds of deposits and a tooth surface. In addition, the tip of the Balamuth device, near where the jet exits the device, is designed to impart some ultrasonic energy to the tooth surface through direct contact. The blunt tip of the device massages the tooth and gingival surfaces.

Again, however, the main source of disruptive energy in the Balamuth device is cavitation. Some direct energy is applied as well, although the short, blunt tip of the device is intended for massage and stimulation. To avoid frictional heating of the tooth, which would lead to patient discomfort, the ultrasonic energy is confined to short bursts.

It is also known that constant application of ultrasonic energy can destroy the ultrasonic device tips, especially at bends or curves, where repeated flexing at ultrasonic frequencies causes heating of the tip material.

To overcome some of these deficiencies, U.S. Pat. No. 3,636,947 of Balamuth discloses a tip with a more pointed end that is formed of a strong metal alloy. The tip of this Balamuth is relatively short and wide, and is only slightly angled. It is difficult to reach certain surfaces of the teeth with this tip configuration, however, and metal tips require substantial cooling, usually with a stream of water.

It is well known, and recently used to advantage by toothbrush manufacturers, that the most appropriate shape for a dental tool is not straight, but bent or curved. In addition, where it is desired to reach all surfaces of the teeth and adjoining gingival and periodontal tissues, such as with the metal scalers used by professionals, it is necessary that the tip of the tool have a generally hook-like or crescent-like shape. Attempts to create a slimmer ultrasonic tip with such a shape for home use have been unsuccessful.

To be appropriate for home use, the tips must be inexpensive, interchangeable and preferably disposable. The use of plastics, however, creates other difficulties. A relatively long and slender curved tip would normally melt or fracture at various stress points along the curve or bend when subjected to ultrasonic energy at frequencies preferred for dental hygiene applications.

It is thus an object of the invention to provide an ultrasonic tooth cleaner for home or personal use that removes dental plaque deposits through direct contact of the tooth surfaces and the adjacent gingival and periodontal tissues.

It is a further object of the invention that the tooth cleaner be formed to reach all tooth surfaces in the oral cavity and adjacent soft tissue structures.

It is a further object of the invention that the tooth cleaner be formed of a material capable of withstanding constant ultrasonic energy in the frequency and amplitude ranges desirable for dental hygiene purposes.

It is a further object of the invention that the tooth cleaner be formed of a relatively soft material having properties which permit transmission of ultrasonic energy but—that will not damage tooth enamel or the adjacent gingival and periodontal tissues.

It is another object of the invention that the tooth cleaner have interchangeable and/or disposable tips for interpersonal hygiene.

It is another object of the invention that any part of the tooth cleaner that comes in contact with tooth and adjacent soft tissues not become hot and require more than a minimal stream of cooling fluid.

It is a further object of the invention that therapeutic fluids be dispersed ultrasonically for greater penetration of interproximal regions of the dentition and into gingival crevices and pockets.

It is yet another object of the invention to provide an ultrasonic cleaner tip which satisfies one or more of the foregoing objects and which is shaped to clean broad surfaces such as the dorsum of the tongue.

SUMMARY OF THE INVENTION

In accordance with the objects of the invention, an ultrasonic tooth cleaner is provided having an elongated tip having multiple bends or a curved shape. This shape allows the operator to reach any surface in the oral cavity, and imparts a whipping action as well as a longitudinal component of motion at ultrasonic frequencies. The tips are formed of particular plastic materials that, unlike those made of metal, do not become hot and require little or no cooling, and which can transmit and also withstand constant ultrasonic vibration in a frequency and amplitude range that is therapeutically desirable and beneficial. Tip apertures are suitably shaped to prevent the spray generated ultrasonically from coalescing and causing the dripping that would make such a device unsatisfactory for consumer use.

The foregoing and other objects and advantages of this invention will become apparent to those skilled in the art upon reading the detailed description of a preferred embodiment in conjunction with a review of the appended drawings.

BRIEF DESCRIPTION OF THE DRAWINGS

FIG. 4 is a cross-sectional view of another tooth cleaner tip according to the present invention;

FIG. 5 is a cross-sectional view of yet another tip according to the present invention; and FIG. 6 is a view, partially in section, of yet another tip according to the present invention.

DETAILED DESCRIPTION OF THE PREFERRED EMBODIMENTS

Figure 1:
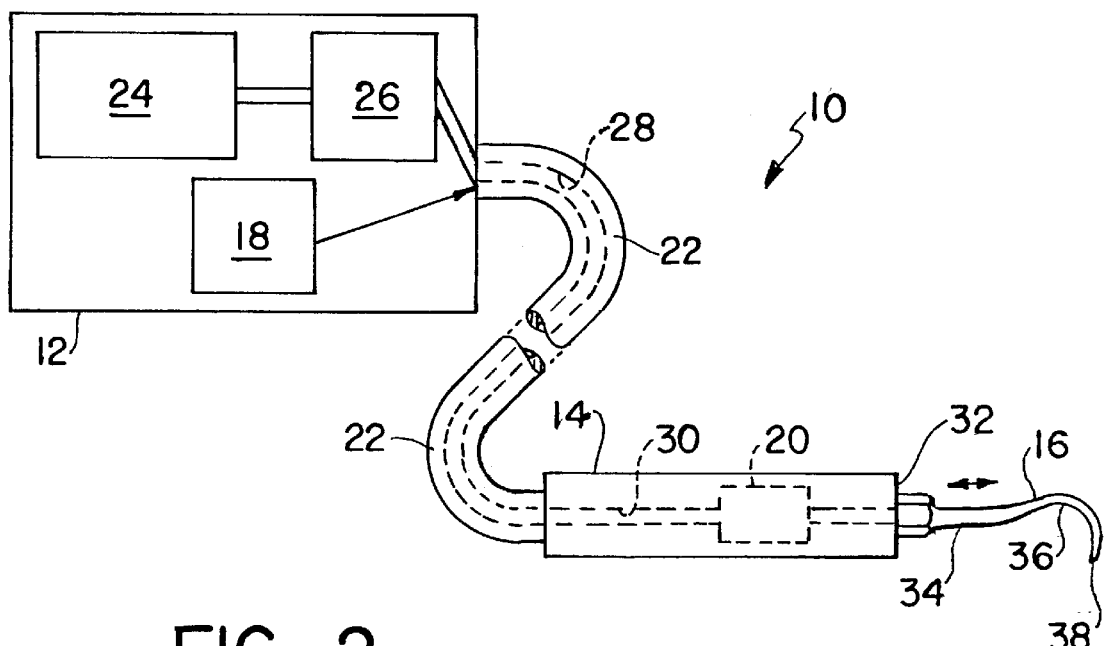
FIG. 1 is a perspective view of an ultrasonic tooth cleaner according to the present invention.

Referring now to the drawings, FIG. 1 shows an ultrasonic tooth cleaner 10 chiefly comprised of a base 12, a handle 14, and a cleaner tip 16. The base 12 comprises electrical or other systems 18 for controlling the ultrasonic driver 20 of the handle 14. The handle 14 comprises any known ultrasonic driver 20, such as the magnetic coil system disclosed in U.S. Pat. Nos. 3,547,110 and 3,636,947, the disclosures of which are hereby incorporated by reference as if set forth in their entirety herein. Other drivers, such as fluid pressure or air/piston or piezoelectric driven systems and the like will work similarly. The handle 14 is attached to the base 12 through a tube 22 that carries the necessary energy, whether it is electrical, pneumatic or hydraulic, to the handle 14 to control the driver 20. It is further described below that a fluid delivery system is preferably incorporated within the tooth cleaner 10. Thus, base 12 preferably further comprises a fluid reservoir 24 and pump 26, while the tube 22 includes a fluid passageway 28 leading to an internal channel 30 in the handle 14. Alternatively, the pump 26 could be replaced with a pressurized fluid source, such as a bottle of carbonated water (not shown). Upon actuation of a valve on the bottle, the pump or the carbonation would propel the fluid contents through the passageway 28 and through the cleaner tip 16 to facilitate debris removal and tooth cleansing. The bottle may also be refillable and resealable.

The cleaner tip 16 is removably received in the distal end 32 of the handle 14 such that it will be mechanically coupled to the ultrasonic driver 20 of the handle 14. The tip 16 may also be coupled in fluid communication with fluid delivery channel 30, if present. It is preferred that the tip 16 be held within the handle 14 with either a threaded or bayonet-type mounting collar 54 (as seen in FIG. 4) to prevent accidental ejection during vibration, but to allow quick and simple mounting and removal, or interchangeability.

Figure 2:
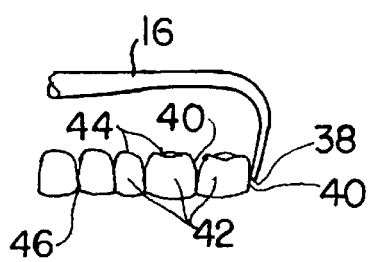
FIG. 2 is a detail plan view of a tooth cleaner tip according to the present invention engaging a tooth surface.

The tip 16 is preferably shaped with a straight portion 34 adjacent the handle and a curved portion 36 extending to its distal end 38. The curved portion 36 preferably has a sufficient curvature so that the distal end 38 will be facing at approximately a right angle to the straight portion 34. This allows the tip 16 to engage poorly accessible areas, even the rear-facing surfaces 40 of many of the rear molar teeth 42 within the oral cavity (as shown in FIG. 2, it being understood that the rear of the oral cavity is to the right). The tip 16 is also preferably long enough such that the distal end 38 of the tip 16 can engage the rearmost surface of any tooth without requiring any portion of the handle 14 to be inserted into the oral cavity.

Because of the extensive curve of the tip 16, and the required length, it is preferred that the tip have a narrow cross-section, such as having a width only a few percent of its length. This avoids having a large amount of material within the user's mouth during cleaning, which would make it somewhat difficult for the user to visually monitor the cleaning process which might make tooth cleaning uncomfortable and therefore less likely to be done regularly.

In addition, the tip 16 should have decreasing mass toward its working distal end 38, to further magnify the amplitude of ultrasonic vibration. Also, the aperture of the distal working end should be enlarged over a distance of 0.5 to 1.5 mm from the distal end 38 to prevent coalescence of the ultrasonically dispersed fluid spray upon emission from distal and 38.

In operation, the distal end 38 of the tip 16 is engaged to a tooth surface 40,44, while the base 12 controls the ultrasonic driver 20 within the handle 14 to oscillate the tip 16 at ultrasonic frequencies. Preferably, the tip 16 oscillates along the axis of the handle 14 at approximately 20,000 Hz to 50,000 Hz, although other frequencies may be suitable. This ultrasonic energy is then directly transferred to deposits on the surface 40,44 of the tooth 42. The energy will also tend to travel to the immediately adjacent area of the deposits and tooth 42. This energy causes the disruption of the mechanical and chemical bonds formed among the various plaque intercellular components, its bacteria, and between plaque and the tooth surface. Disruption (destruction) of other chemical and mechanical bonds between soft deposits and the surface is believed to take place, as well as bacterial cell lysis caused by cavitation.

The distal end 38 of the tip 16 is moved around the surface of the various teeth 42 and to the interproximal areas 46. Due to its slender and bluntly pointed distal end 38, it is possible for the tip 16 to slightly penetrate the subgingival area of the teeth, although not so far as to cause damage. When engaged to the tooth near or directly on the gingiva, the blunt tip will massage the gingiva without damaging its tissue.

Due to the length of the tip and the constant application of ultrasonic energy, the tip 16 should be formed of a filled or unfilled composite polymer, such as a mixture of reinforced resins manufactured under the trademarks DELRIN, NORYL and LEXAN. DELRIN is an acetal resin type plastic that offers a high balance of strength and stiffness with a high fatigue endurance. NORYL is a polyphenylene oxide type plastic that has high heat and impact resistance. LEXAN is a polycarbonate resin that has high strength and heat resistance. Such materials are able to withstand the high stress and energy produced with constant ultrasonic vibration without excessive heating, particularly at the points along the bends.

A presently preferred material for construction of the tip 16 is an amorphous thermoplastic polyetherimide manufactured under the trademark ULTEM by General Electric Co.

The tip material should preferably have hardness much less than that of tooth enamel and must be able to transmit ultrasonic energy in the desired frequency and amplitude ranges. Thus, regardless of the force applied by the operator, no erosion of the tooth will occur. Other composite or polymer materials, such as glass-reinforced resins, may be similarly used if they meet the requirements stated above. With any of the foregoing plastics and other similar polymer materials, the tips can be mass-produced so that they may be cost-effectively disposable and any given household can have at least one tip for each family member. The important consideration in the selection of the particular plastic to be used is the ability to transmit ultrasonic energy within the frequency range and at an amplitude which is therapeutically desirable and beneficial.

To cool the frictionally heated surfaces at the point of contact 48 between the tip 14 and the tooth surface 40,44, it is preferred that the tip 16 have a central bore 50 running substantially along its entire length to be supplied with a fluid flow from the channel 30 in the handle 14 while in operation, as mentioned above. It is also preferred that the aperture of the distal end of the tip be enlarged to avoid coalescence of the fluid exiting from the central channel other than in the form of a fine ultrasonically generated spray. Such coalescence results in dripping which is unsatisfactory for use of the tooth cleaner device by the user. The fluid serves the several purposes of cooling the tip 16 and the point of contact 48 with the tooth, as well as flushing away the deposits loosened by the ultrasonic energy, and also allows for the cavitation effect which can break plaque and cause bacterial cell lysis. This fluid may be water, or for greater effect, is preferably one of a number of bacteriostatic, bactericidal, anti-metabolic or cell lysis compounds. The fluid can also contain anti-malodor compounds such as zinc salts and sodium peroxide since poorly accessible sites in the mouth, such as the dorsum of the tongue and embrasures, gingival crevices and occlusal fossae of the dentition, are major sites of oral bacterial putrefaction and such malodor compound generation.

Figure 3:
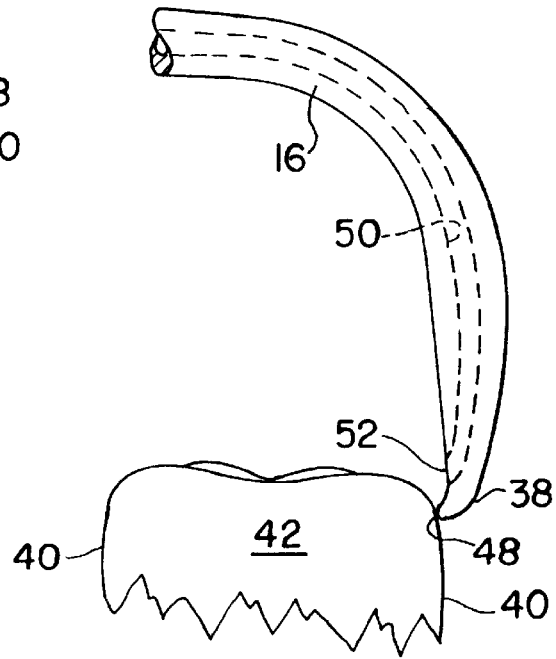
FIG. 3 is a detail view of the distal end of a tooth cleaner tip engaging a tooth surface.

As shown in FIG. 3, the fluid may flow from an outlet 52 adjacent the extreme distal end 38 of the tip 16 or from an outlet 52' at the extreme distal end 38' of the tip 16' as shown in FIG. 4. When at the extreme distal end 38' it can be seen that the fluid flow will act as a cushion between the tip 16' and the tooth.

The fluid may also serve as an additional energy carrier, transmitting some of the ultrasonic energy from the tip 16 to the surrounding area, as is known.

As most easily seen in FIG. 4, the preferred method of forming the central bore 50' is to drill the two ends and meet at the position marked A. Of course, the distal portion of the bore 50' would be drilled before the tip 16' is bent into its final shape. This method simplifies forming the internal threads 54 or other mounting structures that are needed.

It is contemplated that the curvature of the tip 16 could not be gradual over its entire length, but rather concentrated near the distal end. In other words, the straight portion 34 would be a majority of the tip 16, rather than the curved portion 36. The curvature may also not be smooth, but include multiple angled bends 56 at different points along the tip 16', such as is shown in FIG. 4. It is preferred that these angled bends 56 would be in opposite directions to return the distal end 38' to a convenient position generally along the axis of the handle. In either case, the complex shapes of the tip allow for easier handling and better access to all tooth surfaces.

With reference now to FIG. 5, a tip 16" is shown provided with a head or disc 60 at the distal tip 38". The disc 60 provides a broad, dispersive surface for use on oral surfaces such as the dorsum of the tongue, a significant site of oral malodor generation. The dispersive disc 60 enhances the cushion action of the fluid which separates the operator's tongue, for example, from the tip 16". The disc 60 preferably has a central aperture 62 to permit fluids to flow through the central bore 50" and out of the central aperture 62. Preferably, the central aperture 62 is slightly smaller than a bore 52" at the distal tip 38" to ensure a good bond between the distal tip 38" and the disc 60. For example, a 0.025 inch diameter disc 60 may be provided with a 0.063 inch aperture 62 when the bore 52" in the tip 16" is 0.064 inches. The disc is preferably 0.039 inches thick, and may be cut from a rod of material, such as Ultem 1000. The disc 60 may be applied to the distal tip 38" by solvent bonding techniques. For example, the disc 60 may be centered and pressed flush onto the tip 38" and attached by applying a solvent such as methylene chloride (dichloromethane) with a glass hypodermic syringe. The solvent will dry in about an hour. This solvent is available from Baker Chemical Co., Phillipsburg, N.J. 08865. The tip 16" of this embodiment can be used to apply ultrasonic energy to other areas of the body such as skin wounds.

To improve and/or enhance the ability of the cleaner tip 16 or 16' to remove plaque and bacteria from the more inaccessible interproximal sites, an extension segment 70 may be secured to the distal end 38, 38' of the cleaner tip 16, 16'.

The extension segment provides an enlarged cavity 72 distal to the distal 38, 38' within an inlet of the extension segment 70 at a proximal end 74 thereof. The extension segment 70 may be secured by a simple compression fit of the proximal end 74 over the distal end 38, 38' for slip-on attachment to the cleaner tip 16.

The cavity 72 communicates with a distally extending fluid channel 76 to a distal tip 78. Preferably, the distal tip 78 defines an aperture about 0.5 mm in diameter, and the channel 76 is preferably 5 to 25 mm long to provide a toothpick-like structure. Such a construction has empirically been found to not affect ultrasonic action or cause undesirable coalescence of the spray. In particular, a malodor challenge test was performed in which the amino acid cysteine was introduced using a fine pipette into an interproximal site of a patient's mouth. Any bacteria contained in the plaque which adheres to the tooth and adjoining soft tissue rapidly catabolizes the cysteine and produces volatile sulfur compounds which are then measured using a halimeter. Use of the tip segment 70 provided improved cleaning of such generally inaccessible regions. The extension segment 70 may be disposable or reusable and preferably is made of the same material as the cleaner tip 16, 16'. Because the cleaner tip 16 prime and the tip segment 70 are made of plastic or other non-metallic materials, the ultrasonic flossing device can be used with dental implants without risk of damaging the titanium used for the implant.

By inhibiting the formation of volatile sulfur compounds, for example, by operating the ultrasonic flosser of FIGS. 1–6 with a fluid solution containing zinc (such as viadent), the halimeter reading can be maintained below an objectionable level, e.g., 25, for a period extending up to about four hours.

While the embodiments of the invention shown and described are fully capable of achieving the results desired, it is to be understood that these embodiments have been shown and described for purposes of illustration only and not for purposes of limitation.

What is claimed is:

1. An ultrasonic cleaner for removing deposits from a dorsal surface of a tongue, comprising:

a handle having an ultrasonic driver;

a cleaner tip coupled to and being oscillated by said ultrasonic driver, said tip having a distal end and being shaped such that said distal end is generally perpendicular to said handle, said tip being formed of a polymer material capable of transmitting constant ultrasonic vibrations from said driver;

a dispersive head connected to said cleaner tip, said head extending in a plane generally perpendicular to said cleaner tip and being oscillated by said ultrasonic driver.

2. A cleaner as in claim 1, further comprising:

a base connected to said handle, said base controlling said ultrasonic driver and supplying fluid flow to said handle, said handle having an axial channel for receiving said fluid, said cleaner tip and said dispersive head each having a central bore for receiving said fluid from said handle and delivering said fluid approximately at said distal end.

3. A cleaner as in claim 1 wherein said dispersive head is also formed of a polymer material capable of withstanding and transmitting constant ultrasonic vibrations from said driver.

4. A cleaner as in claim 1 wherein said dispersive head and said cleaner tip are formed from the same polymer material.

5. A cleaner as in claim 1 wherein said dispersive head and said cleaner tip are formed from different polymer materials.

6. A tooth cleaner as in claim 1 wherein said polymer material has a hardness less than that of tooth enamel.

7. An ultrasonic tooth cleaner as in claim 6, further comprising:

a base connected to said handle, said base controlling said ultrasonic driver and supplying fluid flow to said handle, said handle having an axial channel for receiving said fluid, said cleaner tip having a central bore for receiving said fluid from said handle and delivering said fluid approximately at said distal end.

8. An ultrasonic tooth cleaner for removing deposits from a tooth surface, adjoining soft tissues, or both and ultrasonically providing therapeutic and other dental hygiene fluids thereto, comprising:

a handle having an ultrasonic driver for creating ultrasonic vibrations and an axial channel for receiving a fluid and imparting said ultrasonic vibrations thereto;

a base connected to said handle, said base energizing said ultrasonic driver and supplying said fluid to said handle;

a cleaner tip removably coupled to and being oscillated by said ultrasonic driver, said tip consisting essentially of a polymer material capable of transmitting constant ultrasonic vibrations from said ultrasonic driver and having a distal end and a channel for receiving said fluid from said handle and delivering said fluid as an ultrasonically dispersed fluid spray approximately at said distal end, said tip including an bore at said distal end which is enlarged relative to said channel, said bore having a size sufficient to prevent coalescence of the ultrasonically dispersed fluid spray upon emission from said distal end.

9. A tooth cleaner as in claim 8, wherein said cleaner tip is gradually curved and is formed of a composite resin.

10. A tooth cleaner as in claim 8 wherein said polymer material has a hardness less than that of tooth enamel.

11. A tooth cleaner as in claim 8, wherein said cleaner tip is elongated in an axial direction such that said distal end contacts a rearmost tooth within an oral cavity without any portion of said handle being within said oral cavity.

12. A tooth cleaner as in claim 8, further comprising a plurality of said cleaner tips interchangeably coupled to said handle.

13. A disposable cleaner tip for an ultrasonic tooth cleaner of the type having a vibrating portion and which delivers a fluid, comprising:

an elongated, plastic housing having an axial channel extending from a proximal end to a distal end, said channel emitting a fluid spray delivered by said ultrasonic tooth cleaner, said proximal end being shaped to be removably coupled to said ultrasonic tooth cleaner, and said channel including a bore at said distal end which is enlarged relative to said axial channel, said bore having a size sufficient to prevent coalescence of the fluid spray upon emission from said distal end.

* * * * *